Jan. 18, 1966 H. R. MARTIN Plant Pat. 2,588
PEACH TREE
Filed Dec. 23, 1963
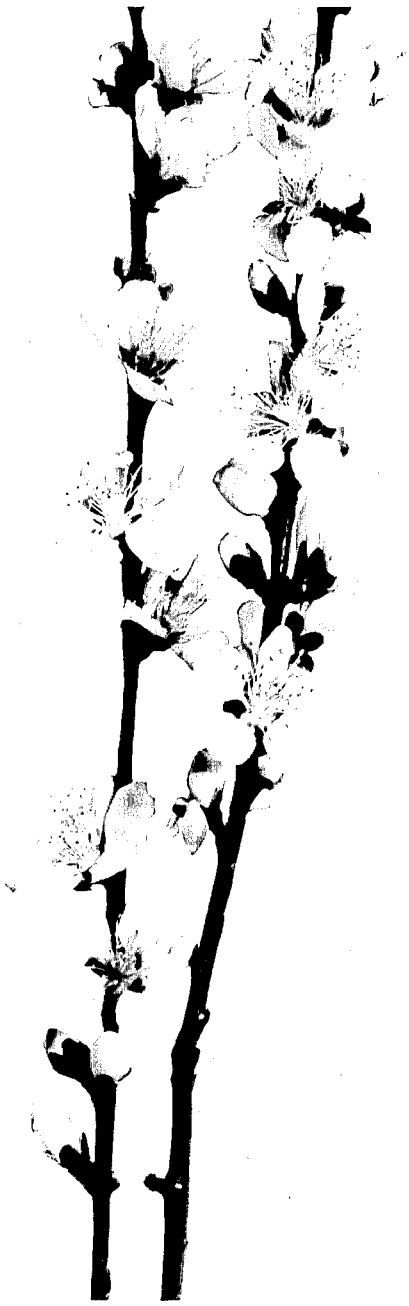
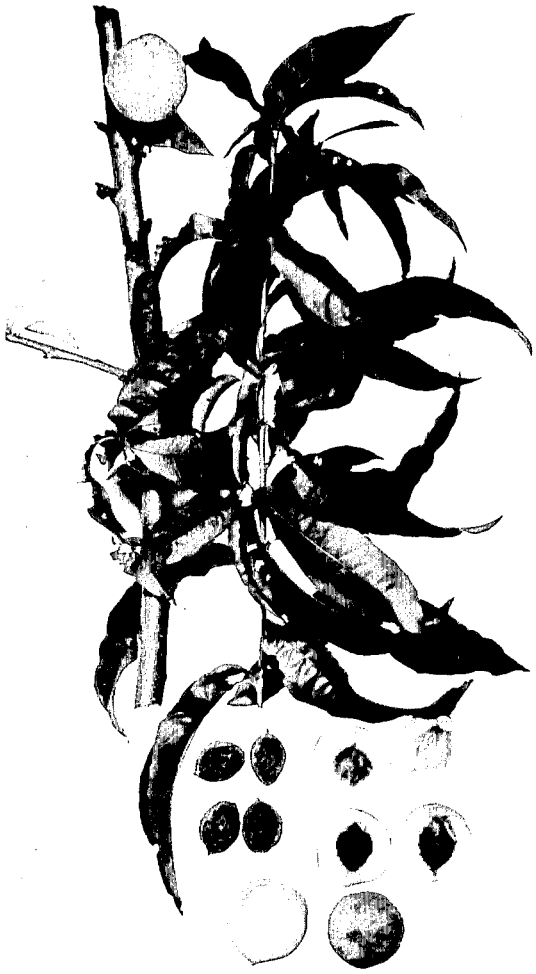
HAROLD R. MARTIN
INVENTOR
Huebner & Worrel
ATTORNEYS United States Patent Office Plant Pat. 2,588
Patented Jan. 18, 1966

2,588
PEACH TREE

Harold R. Martin, McFarland, Calif., assignor to Fortuna Trees, McFarland, Calif.

Filed Dec. 23, 1963, Ser. No. 332,985
1 Claim. (Cl. Plt.—43)

The present invention relates to a new and distinct variety of peach tree characterized by its early, profuse, and regular bearing habits, whose seeds are advantageously employed in the propagation of seedlings for use as rootstocks; such seedlings being particularly characterized by good resistance to rootknot nematodes.

Peach tree roots are notoriously subject to damage by rootknot nematodes, particularly *Meloidogyne incognita acrita* and *Meloidogyne incognita javanica*. Infection of trees by such nematodes has caused such widespread damage as to necessitate the removal of entire orchards. In the development of a rootstock having improved resistance to such nematodes, other undesirable characteristics were recognized in the common rootstocks. Such characteristics include weeping, excessive sucker growth at budding height, lack of vigor, or obviously monster hybrids of unsual vigor, bark abnormalties which hinder budding, abnormal or unwanted root structure. and crown gall or suspicious root lesions. Undesirable characteristics of peach trees employed to produce seeds for seedling rootstock include double blossoms which hinder pollination and seed setting, defective stigmas, clingstones and willowy branches which hinder pruning and picking operations.

An object of the present invention was, therefore, to produce a peach tree characterized by the production of seeds which when germinated produce seedlings having good resistance to nematode infection, an absence of bark abnormalities, abnormal root structures, crown gall, and other root lesions.

Another object was to provide a peach tree which produces seeds which when germinated result in seedlings having vigorous and uniform growing habits.

Another object was to produce a peach tree which produces seeds which when germinated result in seedlings having a minimum of suckers, thus facilitating nursery work and budding.

Another object was to produce a peach tree characterized by the production of seeds which when germinated result in fast growing seedlings which attain a larger size at budding time than conventional seedlings to permit early and complete June budding.

Another object was to provide a peach tree which is a regular and heavier bearer of freestone fruits suitable for seedling production.

Another object was to provide a peach tree which produces seeds characterized upon germination by the production of seedlings having an upright growing habit for easier orchard working.

Another object was to provide a peach tree having single flowers for improved pollination and seed setting.

The attainment of the foregoing and other objects and advantages will become more fully apparent upon reference to the drawing and following description.

The drawing shows specimens of blossoms, branches, leaves and characteristic fruit, a peach cut transversely of the suture plane and open for inspection of both resultant halves, a peach cut on the suture plane and likewise opened for inspection, and characteristic stones or seeds, all of the new variety.

The instant variety of peach tree resulted from a planned and deliberately followed procedure directed to obtaining an improved peach tree for producing seeds for seedlings having the above described characteristics. Approximately 4,000 seedlings were raised near the city of McFarland, county of Kern, State of California, from seeds harvested from ten parent trees selected from the F–2 generation of the Rancho Red Leaf Peach Tree #17, a seedling of the variety described in Plant Patent No. 1,440. Such seedlings were subjected to a process of elimination of all seedlings possessing undesirable characteristics, from which 150 seedlings were retained for further evaluation as potential parent trees. Seed from 49 of the 150 trees which were subject to the same elimination process as their parent trees was obtained in 1960. This seed was designated F–3 and was tested in tanks, and under nursery conditions at Wasco, California. One seedling showed its superiority over the parent trees on all major characteristics.

The selected single superior seedling was asexually reproduced by budding scions taken from the seedling into 106 seedlings of the Lovell unpatented peach trees. The resultant trees having Lovell seedling roots and tops of the subject variety were grown and carefully observed. The characteristics described herein found in the original seedling were also found in the tops of these budded trees. Fruit was produced from the original seedling and from the budded trees, the seeds were removed from these fruit, the seeds were germinated, and a new generation of seedlings was produced. These new generation seedlings then had their tops budded to Nonpareil almonds, Fortuna clings, Cortez clings, Vivian clings, and Sunrise nectarines. Three-hundred and fifty of the Nonpareil almond budded trees on the new generation seedlings were planted ten trees to each of 34 lots in the center of a forty-acre orchard of Nonpareil almonds budded to unpatented Nemaguard trees of the same age at Wasco, California. For control purposes, there were also ten trees of Nonpareil almonds budded on Lovell unpatented rootstock in the same orchard. After one year of growth, the majority of the lots of trees on the new generation seedlings were doing as well or better than those on the Nemaguard and Lovell rootstock and were distinctly superior in growth and bud union compatibilty. The lots budded to the cling peaches were planted in Tipton, California, as replants across a 160-acre 30 year old cling orchard. These were planted in areas where replants of the S—37 peach tree of Plant Patent No. 904 had previously died. After one year, the cling peach trees on said new generation seedlings were doing well, considering the difficulty of establishing replants in an old orchard. In April 1962, scions from the instant variety were June budded to a selection of miscellaneous year-old Rancho Red Leaf seedling trees near McFarland, California. In May 1963 scions from the instant variety were June budded to seedlings from a rootstock known as the Rancho Resistant, U.S. Plant Patent No. 1,941 at Wasco, California. Fruit produced from the original superior seedling of the subject variety and that from the subject variety budded onto other rootstock has been produced in substantial volume, the seeds removed therefrom, and the seeds germinated to produce seedlings. The subject variety is characterized by the production of such seedlings which are substantially uniform in their fast, vigorous growth, attaining a larger size in time for June budding than most other known seedlings. Such seedlings have also proved to have outstanding nematode resistance. The trees of the subject variety have proved to be desirable sources for seeds for seedling production in that they have blossoms which are late, single and pollinate readily; the trees produce more regularly and more heavily than varieties usually employed for seedling production purposes; and they are upright in their growing habits, facilitating their care and budding in the nursery.

Seeds from the asexually reproduced progeny of the subject variety in 1961 and 1962 were sent to the University of California at Davis, California, to evaluate the resistivity of seedlings of the subject variety to nematodes. During such tests, tanks of sterilized soil were prepared, the soil of one group of tanks being impregnated with *Meloidogyne incognita javanica* nematode culture and that of another group of tanks with *Meloidogyne incognita acrita* nematode culture. Seeds produced by the subject variety, by Lovell and by Nemaguard peach trees were sown in each of the tanks in individual rows, germinated, and grown for the same period under precisely identical cultural conditions. The seedlings were dug at the same time and their roots carefully inspected and graded with respect to nematode infection in accordance with the following scale:

0—No infection found
1—Slight galling
2—Moderate galling
3—Damaging galling
4—Severe galling
5—Completely infected The following results were noted as being representative of the many tests conducted:

SOIL IMPREGNATED WITH *MELOIDOGYNE JAVANICA*

| Row | Variety from which seedlings were derived | Number trees | Aver. height | Aver. grade |
|---|---|---|---|---|
| 6 | Subject variety | 18 | 63 | 2.1 |
| 4 | Nemaguard | 19 | 67 | 2.3 |
| 1 | Lovell | 11 | 39 | 4.2 |
| 24 | do | 19 | 58 | 3.6 |

SOIL IMPREGNATED WITH *MELOIDOGYNE INCOGNITA ACRITA*

| | | | | |
|---|---|---|---|---|
| 6 | Subject variety | 16 | 103 | 0 |
| 4 | Nemaguard | 20 | 107 | 0.9 |
| 1 | Lovell | 2 | 37 | 4.0 |
| 24 | do | 2 | 30 | 5.0 |

These results showed that the seedlings derived from trees of the subject variety have a resistance to *Meloidogyne incognita javanica* and *Meloidogyne incognita acrita* nematodes substantially better than the Lovell seedlings and as good as or possibly slightly better than the Nemaguard seedlings. Furthermore, the results of the tests showed the average heights of the seedlings derived from the subject variety at the time of the tests to be substantially greater than the average heights of the Lovell seedlings and nearly equal to the average heights of the Nemaguard seedlings.

Referring more particularly to the pomological details of the new and distinct variety of peach tree, with all major color identifications being by reference to Maerz and Paul Dictionary of Color, the following characteristics occurring under the ecological conditions prevailing at the designated location of the asexual reproduction are noted:

Parentage: The seed parent was the seedling known as Rancho Red Leaf #17, which was a selected seedling of the Rancho Red Leaf, Plant Patent No. 1,440 and the other parent is unknown.

Tree:

*Size.*—Normal standard, approximately 15′ diameter at maturity.

*Figure.*—Form and density controlled by pruning but tends to be conical with limbs markedly drooping when weighted by crop but returning to upright positions when relieved of weight.

*Productivity.*—Highly productive and profuse bearer under standard orchard conditions producing an average of 1,000 seeds in its second bearing year compared to Lovell with approximately 540 seeds in its second bearing year and Rancho Resistant's 390 seeds.

*Trunk.*—From 4⅝ to 6⅜″ at ground level when mature and having a first year growth of approximately 8′ and a second year growth of approximately 5′, with a semi-rough surface having no appreciable deep grooves or ridges. Silvery brown-black in color, somewhat lighter in shade than Rancho Resistant, Plant Patent No. 1,941, and less brown than Lovell branches.

Branches:

*Size.*—Long and slender; normally upright except when laden with crop.

*Surface.*—Smooth, circular, and even.

*Color.*—Green (19–L–3) when young to reddish brown (15–E–8) at maturity.

*Lenticels.*—Approximately 55 to the square inch of a size 1/64″ to ⅛″.

Leaves:

*Size.*—Markedly varying but generally medium when mature.

*Length.*—Average 4″ to 5″.

*Width.*—Average 1½″.

*Shape.*—Lanceolate with acuminate tip.

*Color.*—Upper side—yellowish-green (22–L–6); lower side—lighter yellowish-green (22–K–3).

*Marginal form.*—Crenate.

*Glandular characteristics.*—Minute reniform, confined principally to juncture of leaves and petiole.

*Petiole.*—Length—medium to short, dark red in color (5–G–5) on under side and on the upper side light green (20–L–4).

Blossom buds: Medium large, long, free, pubescent.

Blossoms:

*Date of bloom.*—Late, averaging March 10, approximately one week after Lovell and three days after Rancho Resistant.

*Size.*—Large, single.

*Color.*—From pale pink (3–B–1) to light pink (4–C–2) with streaks of darker pink (4–K–1) from base of petals.

Fruit:

*Maturity.*—Picking ripe, average August 20.

*Size.*—Unusually uniform. Longitudinal diameter—average 2″. Diameter transversely in suture plane—average 1¾″. Diameter transversely in plane at right angles to suture plane—average 2″.

*Form.*—Consistent, usually symmetrical. Suture—distinct, shallow, extending from stem to pistil point. Ventral surface—slightly lapped with laps substantially equal. Stem cavity—substantially shallow. Base—globular. Apex—globular with minute pistil point. Stem—short, stocky, relatively firmly affixed to pit.

Skin:

*Thickness.*—Thick, tough.

*Tendency to crack.*—None observed.

*Color.*—Reddish-brown (4–D–11) to yellowish-orange (11–L–4).

*Pubescence.*—Considerable.

Flesh:

*Color.*—Light yellowish-green (18–G–1).

*Surface of pit cavity.*—Rounded, average depth 1″; average breadth approximately ¾″; average thickness ⅝″.

*Color of pit well.*—Reddish-brown (5–L–8) medium brown (6–G–10).

*Amygdalin.*—Present.

*Juice.*—Abundant.

*Flavor.*—Poor.

*Aroma.*—Lacking.

*Texture.*—Course.

Stone:

*Free of cling.*—Markedly free.

*Fibers.*—Few adherent.

*Size.*—Average length 1″; average breadth ¾″; average thickness ⅜″.

*Form.*—Obovate.

*Hilum.*—Oval.

*Apex.*—Minutely acuminate.

*Sides.*—Symmetrical.

Stone (continued):

*Surface.*—Regularly grooved.

*Color.*—Medium brown (7–C–10).

*Splitting tendency.*—Negligible.

*Taste of kernel.*—Mildly bitter.

Use: Production of seeds for rootstock seedlings.

Resistance to disease: Good resistance to nematode infections, crown gall, and root lesions.

It is to be understood that the tree herein described, its fruit, and its progeny may vary in certain respects due to variations in climate, soil or other environmental conditions but that such variations should not obscure the identity of the new variety as set forth in the claim which should be accorded its full scope so as to embrace all of the defined peach trees even when subjected to such ecological variations.

Having thus described and illustrated my new variety peach tree, what I claim as new and desire to secure by Letters Patent is:

A new and distinct variety of peach tree of the freestone fruit type substantially as herein shown and described, characterized particularly by greater production of seeds as compared with the Lovell (unpatented) peach tree and the Rancho Resistant peach tree of U.S. Plant Patent No. 1,941 and which result in seedlings having good resistance to nematode infection.

No references cited.

ABRAHAM G. STONE, *Primary Examiner.*